US00PP34580P2

(12) United States Plant Patent
Ault

(10) Patent No.: US PP34,580 P2
(45) Date of Patent: Sep. 13, 2022

(54) ***ASTER* PLANT NAMED 'COTTON CANDY'**

(50) Latin Name: *Aster oblongifolius*
Varietal Denomination: Cotton Candy

(71) Applicant: James Robert Ault, Libertyville, IL (US)

(72) Inventor: James Robert Ault, Libertyville, IL (US)

(73) Assignee: CHICAGOLAND GROWS, INC, Glencoe, IL (US)

( * ) Notice: Subject to any disclaimer, the term of this patent is extended or adjusted under 35 U.S.C. 154(b) by 0 days.

(21) Appl. No.: 17/527,243

(22) Filed: Nov. 16, 2021

(51) Int. Cl.
*A01H 5/02* (2018.01)
*A01H 6/14* (2018.01)

(52) U.S. Cl.
USPC ..... Plt./355
CPC ..... *A01H 6/1408* (2018.05)

(58) Field of Classification Search
USPC ..... Plt./355
CPC ..... A01H 5/02
See application file for complete search history.

*Primary Examiner* — Kent L Bell
(74) *Attorney, Agent, or Firm* — Penny J. Aguirre

(57) ABSTRACT

A new cultivar of *Aster* plant named 'Cotton Candy' that is characterized by its uniform, rounded and dense mounded plant habit that remains dense as it broadens with age, its tall plant height, its sticky, aromatic foliage that deters deer or rabbits from browsing, its very good resistance to rust, powdery mildew and lace bug predation when grown in comparison trials with other cultivars of *Aster*, and its inflorescences with ray florets that are medium pink-violet in color aging to light violet in color.

2 Drawing Sheets

Botanical classification: *Aster oblongifolius*.
Variety denomination: 'Cotton Candy'.

BACKGROUND OF THE INVENTION

The present invention relates to a new and distinct cultivar of *Aster*, botanically known as *Aster oblongifolius* 'Cotton Candy', and will be referred to hereafter by its cultivar name, 'Cotton Candy'. 'Cotton Candy' is a new herbaceous perennial suitable for landscape plantings.

The new cultivar is the result of a controlled breeding program conducted by the Inventor in Glencoe, Ill. The intent of the program is to develop new cultivars of *Aster* that are hardy in U.S.D.A. Zone 5, resistant to powdery mildew and rust, unpalatable to deer and rabbits, and provide a diversity of desirable flower traits and plant habits.

The new cultivar arose from a cross made in September of 2011 between unnamed and unpatented plants of *Aster oblongifolius* from the Inventor's breeding program as both the female and male parent. 'Cotton Candy' was selected as a single unique plant from the resulting seedlings of the cross in October of 2015.

The new cultivar was first asexually propagated by shoot tip cuttings by the Inventor in Glencoe, Ill. in June of 2016. Asexual propagation by shoot tip cuttings and division has determined that the characteristics of this cultivar are stable and are reproduced true to type in successive generations.

SUMMARY OF THE INVENTION

The following traits have been repeatedly observed and represent the characteristics of the new *Aster*. These attributes in combination distinguish 'Cotton Candy' as a unique cultivar of *Aster*.

1. 'Cotton Candy' exhibits a uniform, rounded and dense mounded plant habit that remains dense as it broadens with age.
2. 'Cotton Candy' exhibits a tall plant height.
3. 'Cotton Candy' exhibits sticky, aromatic foliage that deters deer or rabbits from browsing.
4. 'Cotton Candy' exhibits very good resistance to rust, powdery mildew and lace bug predation when grown in comparison trials with other cultivars of *Aster*.
5. 'Cotton Candy' exhibits inflorescences with ray florets that are medium pink-violet in color aging to light violet in color.

The seed parent of 'Cotton Candy', differs from 'Cotton Candy' in having a shorter plant height and less wide plant spread, an irregular and open plant habit, and an earlier and longer blooming period. The male parent of 'Cotton Candy' differs from 'Cotton Candy' in having ray florets that are medium violet in color, strongly upturned and curled, and fused 50% of their length, and susceptibility to rust. 'Cotton Candy' can be most closely compared to *Aster oblongifolius* varieties 'Raydon's Birthday Pink' (not patented) and 'Dream of Beauty' (not patented). Both cultivars are similar to 'Cotton Candy' in having ray florets that are pink-violet in color and in producing sticky, aromatic foliage that deters rabbits and deer. 'Raydon's Birthday Pink' differs from 'Cotton Candy' in having more ray florets per capitulum, ray florets that are narrower, a slightly shorter plant height, a wider plant spread, and a more irregular and open plant habit. 'Dream of Beauty' differs from 'Cotton Candy' in having more ray florets per capitulum, a shorter plant height and less wide plant spread, susceptibility to lace bug, and a more irregular and open plant habit.

BRIEF DESCRIPTION OF THE DRAWINGS

The accompanying color photographs were taken in October and illustrate the overall appearance and distinct characteristics of the new *Aster* as grown outdoors in a trial plot in Glencoe, Ill.

The photograph in FIG. 1 was taken of a plant 5 years in age and provides a view of the plant habit of 'Cotton Candy' in bloom.

Figure 1:
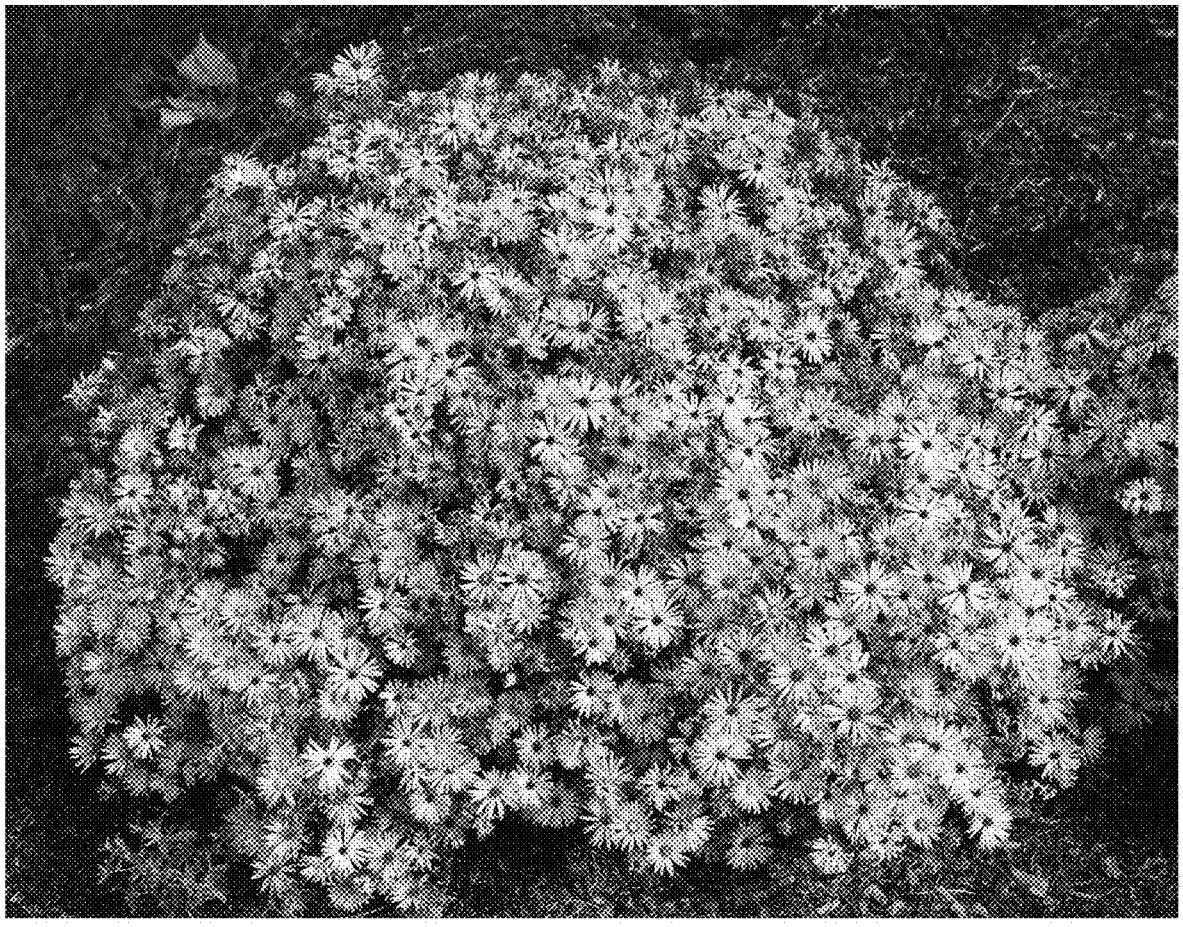
Figure 2:
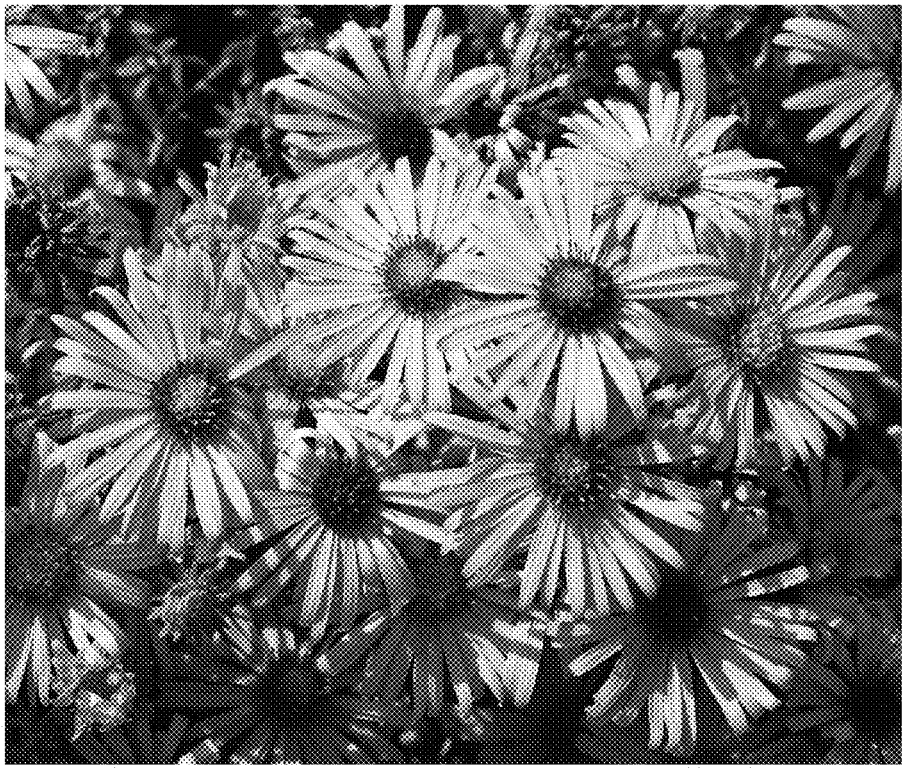

The photograph in FIG. 2 was taken of a plant 2 years in age and provides a close up view of the inflorescences of 'Cotton Candy'.

Figure 3:
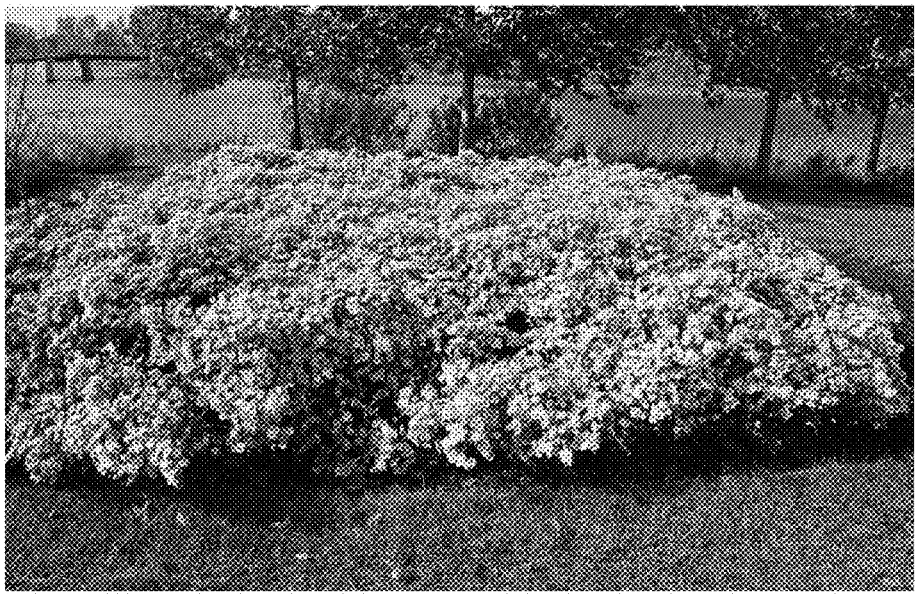

The photograph in FIG. 3 was taken of a group of plants 5 years in age of 'Cotton Candy'.

The colors in the photographs are as close as possible with digital photography techniques available, the color values cited in the detailed botanical description accurately describe the colors of the new *Aster*.

DETAILED BOTANICAL DESCRIPTION

The following is a description of one-year old plants of the new cultivar as grown outdoors in 2-quart containers in Glencoe, Ill. The description of the plant habit and mature height and spread were observed on 3 and 4-year-old plants of the new cultivar as grown in a trial bed in Glencoe, Ill. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming season*.—Typically for 6 weeks commencing in early to mid-September and completing in mid to late October in northern Illinois.

*Plant type*.—Herbaceous perennial.

*Plant habit*.—Uniform, rounded and densely mounded that remains dense as it broadens with age.

*Height and spread*.—An average of 25 cm in height and 40 cm in width as a one-year-old plant in a container, 3-year-old plants grown in the ground; average of 72 cm in height and 122 cm in width, 4-year-old plants grown in the ground; average of 85 cm in height and 160 cm in width.

*Hardiness*.—At least in U.S.D.A. Zones 4 to 7.

*Diseases and pest resistance*.—Has shown very good resistance to powdery mildew (*Golovinomyces asterum* var. *asterum*), rust (*Coleosporium asterum* and *Puccina* sp.) and lace bug (*Corythuca marmorata*) predation.

*Root description*.—Fibrous, 162D in color.

*Propagation*.—Shoot tip cuttings and division.

*Root development*.—4 to 6 weeks to produce a rooted cutting, plants grown from a cutting rooted in June will fill a one-gallon pot and bloom the same year.

*Growth rate*.—Vigorous.

Stem description:

*Stem color*.—New growth; 145A, mature growth; 152A, old wood; a blend of 199A and N199B.

*Stem surface*.—Young stems; matte and glabrous, mature stems; glabrous and glossy.

*Stem size*.—Main stem; about 15 cm in length and 8 mm in width, lateral branches; average of 22 cm in length and 1 mm in width.

*Branching habit*.—1 main stem with an average of 26 horizontal lateral branches, whorled arrangement.

*Branch internode length*.—Average of 1 cm between lateral branches.

Foliage description:

*Leaf division*.—Simple.

*Leaf shape*.—Linear.

*Leaf base*.—Truncate.

*Leaf apex*.—Acute.

*Leaf margin*.—Entire.

*Internode length*.—Average of 4 mm.

*Leaf venation*.—Linear, not conspicuous, midrib recessed on upper surface, coloration same as leaf.

*Leaf attachment*.—Sessile.

*Leaf arrangement*.—Alternate, slightly whorled.

*Leaf number*.—Average of 48 per stem 17 cm in length.

*Leaf surface*.—Both surfaces glabrous, matte and slightly rough to the touch.

*Leaf color*.—Young and mature, upper and lower surface; 144A.

*Leaf size*.—Up to 5 cm in length and 1.5 cm in width.

*Leaf fragrance*.—None.

Flower description:

*Inflorescence type*.—Composite, 1 to 3 capitula per flowering branchlet.

*Lastingness of individual capitula*.—Temperature dependent, under normal field conditions during the fall, typically last about 2 weeks.

*Fragrance*.—Slight and pleasant.

*Quantity of capitula*.—About 30 to 50 per plant as grown in a 2-quart container.

*Capitula buds*.—About 6 mm in depth and 5 mm in diameter, oblong in shape, 143A and NN144A in color.

*Capitula size*.—About 3 cm in diameter and 1 cm in depth, disk is about 1 cm in diameter.

*Peduncle*.—Held at about a 45° angle to flowering branchlet, 1 cm to 3 cm in length and 1 mm in width, N144A in color, surface is matte and densely covered with very short, soft pubescence that matches surface color.

*Involucral bracts* (*phyllaries*).—Whorled around receptacle, average of 30, linear in shape, upper and lower surfaces matte and glabrous and 143A in color, an average of 5 mm in length and 2.5 mm in width.

Ray florets (pistillate):

*Number*.—Average of 35.

*Shape*.—Oblanceolate and linear.

*Aspect*.—Nearly horizontal, slightly downward.

*Size*.—Average of 1 cm in length and 2 mm in width.

*Apex*.—Bluntly acute.

*Base*.—Attenuate.

*Margins*.—Entire.

*Texture*.—Both surfaces smooth, velvety and matte.

*Color*.—When opening upper and lower surface; a blend of 62C and 76A, tips 62D, base NN155D, when fully open upper and lower surface; 76A and 76B, base NN155D.

Disk florets (perfect):

*Quantity*.—Average of 45.

*Shape*.—Tubular.

*Size*.—Up to 3 mm in length and 0.5 mm in width.

*Color*.—22A.

Reproductive organs:

*Presence*.—Disk florets are perfect, ray florets are pistillate.

*Gynoecium*.—Pistil; 1 per disk and ray floret, stigma; bi-lobed, 0.75 mm in length, 22A in color, style; is 7 mm in length, translucent and glossy, NN155A in color.

*Androecium*.—Stamens; 5 per disk floret, fused into tube, 168A in color, acute apex, 0.5 mm in length, anther; 1 mm in length, 200A in color, filament; translucent, 158A in color, pollen; minimal and 21A in color, pappus; made up of thin fuzzy hairs, translucent, NN155D in color, 9 mm in length, ovary; narrow oval in shape, 1.5 mm in length, 0.75 mm in width, 157C in color, glabrous and slightly glossy.

*Fruit and seed*.—None observed to date.

It is claimed:

1. A new and distinct cultivar of *Aster* plant named 'Cotton Candy' as described and illustrated herein.

* * * * *